United States Patent [19]

Garnier

[11] 4,097,223
[45] Jun. 27, 1978

[54] FLASH-TUBE IGNITION SYSTEM

[75] Inventor: John J. Garnier, Hales Corners, Wis.

[73] Assignee: Cutler-Hammer, Inc., Milwaukee, Wis.

[21] Appl. No.: 729,354

[22] Filed: Oct. 4, 1976

[51] Int. Cl.$^2$ .............................................. F23C 3/10
[52] U.S. Cl. ................................ 431/191; 126/91 A; 431/353
[58] Field of Search ............... 126/91, 91 A; 431/353, 431/191, 192

[56] References Cited

U.S. PATENT DOCUMENTS

| 2,041,312 | 5/1936 | Winder et al. | 126/91 A X |
| 2,255,540 | 9/1941 | Dreffein | 126/91 A |
| 3,174,474 | 3/1965 | Jones et al. | 126/91 A |
| 3,220,401 | 11/1965 | Jones et al. | 126/91 A |
| 3,225,757 | 12/1965 | Keller | 431/353 X |

*Primary Examiner*—Edward G. Favors
*Attorney, Agent, or Firm*—Hugh R. Rather; William A. Autio; Michael E. Taken

[57] ABSTRACT

A combustible fuel gas burner has a primary tube supplying gas and primary air to a main burner, a secondary tube supplying secondary air to the main burner to afford complete combustion, and an exhaust tube through which the products of combustion are exhausted. The exhaust tube also acts as a flash-tube for igniting the main burner. In the absence of combustion, the gas and primary air issuing from the primary tube and the secondary air issuing from the secondary tube combine to form an air-gas mixture in the exhaust tube which is too lean (below the lower limit of flammability) to be ignitable. The supply of secondary air is controlled so as to vary the air-gas ratio in the exhaust tube such that this ratio changes through a spectrum of values between the lower and upper limits of flammability wherein the flame propagation speed of the mixture is substantially greater than the flow velocity thereof. A resistance coil is provided at the outlet of the exhaust tube and is energized at an optimum value of the changing ratio, corresponding to an explosive mixture, whereby a flame travels or flashes back to the main burner.

8 Claims, 2 Drawing Figures

FLASH-TUBE IGNITION SYSTEM

BACKGROUND OF THE INVENTION

This invention is in the field of combustible fuel gas burners having flash-tube ignition; and, though not limited hereto, evolved specifically from attempts to provide an automatic reignition system for the burner of a calorimeter.

Natural gas utility companies use calorimeters to determine the heating value or energy content of natural gas for billing purposes and in some cases so that they can either enrich or lean-out a designated quantity of gas. Calorimeters measure the heating value or energy content of a combustible fuel gas by burning the gas at a burner and determining the heat given up to a stream of heat absorbing air passing through a separate tube surrounding the burner by measuring the rise in temperature of the heat absorbing air. The products of combustion of the gas, primary air and secondary air are exhausted through an exhaust tube separate from the heat absorbing air tube. Positive displacement pumps are geared together and provide constant volume delivery of the gas, primary air, secondary air, and heat absorbing air in known proportions whereby the temperature rise of the heat absorbing air can be translated into BTU per cubic foot of the gas.

Such calorimeters are typically used to continuously monitor the heating value of natural gas being pumped from distant drilling stations which are commonly left unattended. A momentary shortage of gas may cause the burner to go out, or, for example, a temporary power failure will stop the pumps and thus extinguish the burner. If the burner goes out, not only is there interruption in the heating value measurement, but also the expense of travel to such station for manual reignition of the burner.

Prior attempts to provide an automatic reignition system included the use of a high voltage spark plug immediately above the burner for energization by flame detection means in response to the absence of a flame. The spark plug was unreliable in operation, however, and its placement interfered with heat transfer to the heat absorbing air and had a variable affect on the calibration of the calorimeter. Attempts to segregate the ignition source from the burning zone have resulted in the present invention wherein the ignition source is placed downstream of the burner, at the outlet of the exhaust tube.

Flash-tube ignition systems for gas burners typically employ a small high velocity gas jet adjacent the inlet of the flash-tube to inspirate surrounding air into the tube to obtain the necessary combustible mixture within the tube whereby an ignitor or pilot burner at the other end (outlet) of the tube ignites the mixture and a flame travels or flashes back to the main burner.

SUMMARY OF THE INVENTION

An object of the present invention is to provide a combustible fuel gas burner with improved flash-tube ignition.

Another object is to provide a burner of the aforementioned character having means for varying the combustible mixture in the flash-tube.

Another object is to provide a burner of the aforementioned character wherein secondary air is controlled such that the flame propagation speed of the mixture in the flash-tube at the time of ignition is greater than the flow velocity thereof.

Another object is to provide a burner of the aforementioned character having an ignition source placed at the outlet of an exhaust tube whereby the exhaust tube also serves as a flash-tube.

One specific object of the present invention is to provide an automatic reignition system for calorimeter burners and the like which is reliable in operation, does not interfere with heat transfer from the flame or with calibration, is downstream of the flame area, and does not require changes in existing burner structures.

Other objects and advantages will hereinafter appear.

DESCRIPTION OF THE PREFERRED EMBODIMENT

Figure 1:
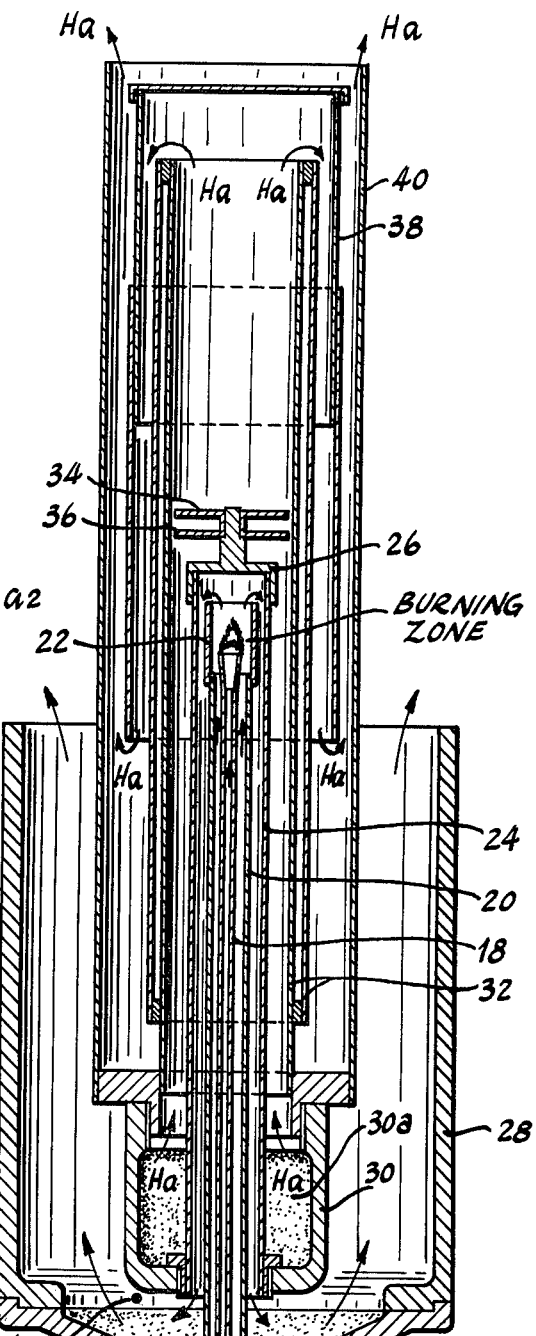
FIG. 1 is a cross-sectional view of a burner constructed in accordance with the invention.
Figure 1:
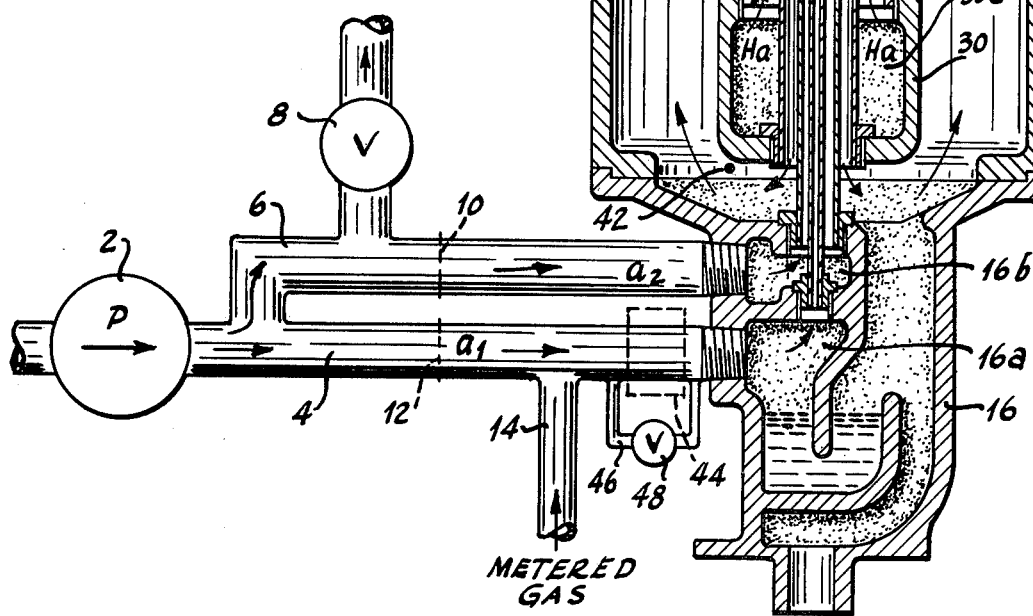

There is shown in FIG. 1 a combustible fuel gas burner assembly used in calorimeter applications.

A positive displacement pump 2 delivers air to parallel supply lines 4 and 6 at a constant rate. Line 4 supplies primary air $a_1$ and line 6 supplies secondary air $a_2$. Line 6 has a control valve 8 which can be opened to vent secondary air to the atmosphere. Each of the supply lines has an orifice for setting the volume flow rate of the air. For example, orifice 10 is sized to produce a flow of secondary air at 1.52 cubic feet per hour, and orifice 12 is 2.6 times smaller to produce a flow of primary air at 0.57 cubic feet per hour. Metered gas is supplied through connection 14 to the primary air supply line at the rate of 0.15 cubic feet per hour to form a gas-primary air mixture $gm_1$, which is fed to the burner.

The supply lines are sealingly connected to the base 16 of the burner. A first cylindrical elongated hollow tube 18 is mounted to the base, extending upwardly therefrom, and has a widened frustoconical top end above which is the burning zone. Mixture $gm_1$ enters a sealed cavity 16a in the base and then travels upwardly through tube 18 to burn at the top thereof as the first cone of a double cone burning zone. A second cylindrical elongated hollow tube 20 is mounted to the base and extends upwardly therefrom, concentrically surrounding tube 18, and has a sleeve 22 extending from the top thereof surrounding the frustroconical portion of tube 18 to form the burning zone. Secondary air enters a sealed cavity 16b in the base and travels upwardly through tube 20 to emerge at the burning zone. Unburned gas remaining after combustion of $gm_1$ at the first cone will mix with secondary air and burn as a second cone.

A third cylindrical vertically elongated hollow tube 24 concentrically surrounds tube 20 and extends above sleeve 22. Tube 24 is sealed at the top by a seal 26 whereby the products of combustion are exhausted downwardly through tube 24 to emerge at the bottom thereof. An open-topped cylindrical hood 28 is mounted to the base and guides the exhaust upwardly to the atmosphere.

There is additionally shown in FIG. 1 means for supplying heat absorbing air around the burner for use in calorimeter applications. A structure 30 is mounted around tube 24 and has a sealed cavity 30a to which air, known as heat absorbing air $H_a$, is delivered at a constant rate by a positive displacement pump (not shown) which is geared with positive displacement pumps supplying gas and primary and secondary air. A cylindrical elongated hollow tube 32, concentrically surrounding tube 24, guides $H_a$ upwardly through perforated baffles 34 and 36 which are mounted to seal 26 in heat transfer relation whereby $H_a$ absorbs the heat given off by the burner flame. A thermometer (not shown) is placed in tube 32 near the top above the baffles to record the elevated temperature of $H_a$. Another cylindrical concentric tube 38 then directs $H_a$ downwardly whereafter another cylindrical concentric tube 40 directs $H_a$ upwardly to the atmosphere.

An ignition source 42, such as a resistance coil, is placed at the outlet of exhaust tube 24 for igniting the burner. When there is no combustion at the burning zone, gas-primary air mixture $gm_1$ will issue from the top of tube 18 and mix with secondary air $a_2$ issuing from the top of tube 20 to form a gas-primary air-secondary air mixture $gm_2$, i.e. $gm_2 = gm_1 + a_2$. Mixture $gm_2$ then flows downwardly through exhaust tube 24 and emerges from the outlet thereof to flow past ignition source 42. Under proper conditions, explained hereinafter, the ignition source can be energized to ignite $gm_2$ whereby a flame travels or flashes back up through tube 24 to the burning zone to thereby ignite the burner. Tube 24 thus serves the dual functions of exhaust and flash-tube.

Valve 8 may be opened and closed in order to variably control the air-gas ratio in mixture $gm_2$ within flash-tube 24 whereby to assure flash-back of the flame. Valve 8 controls secondary air $a_2$, and with valve 8 open, all or most of the air in supply line 6 is vented to the atmosphere whereby little or no secondary air is supplied to tube 20 and thus $gm_2$ contains little or no secondary air, i.e. $gm_2$ approximately equals $gm_1$, and a rich mixture flows in the flash-tube. With valve 8 closed secondary air is supplied to tube 20 and $gm_2 = gm_2 + a_2$, whereby a leaner mixture flows in the flash-tube.

Valve 8 also controls the flow velocity in the flash-tube. For example, with the volume flow rates given hereinbefore, namely, gas = 0.15 cubic feet per hour, $a_1$ = 0.57 cubic feet per hour, and $a_2$ = 1.52 cubic feet per hour, and with valve 8 closed, the flow velocity of $gm_2$ (with $a_2$) in flash-tube 24 is 0.30 feet per second. With valve 8 open, the flow velocity of $gm_2$ (without $a_2$) is 0.08 feet per second.

The ratio of air to gas in $gm_2$ and the flow velocity of $gm_2$ are critical parameters for flash-back ignition because flame propagation speed is a function of the air-gas ratio and the flame propagation speed in one direction should be greater than the flow velocity in the other direction.

Figure 2:
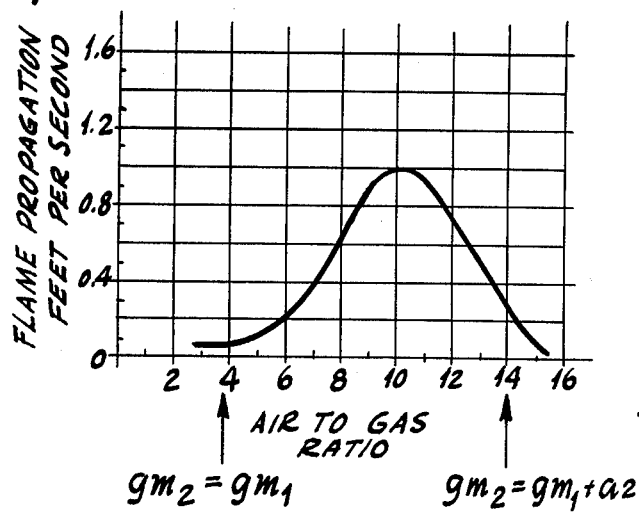
FIG. 2 is a graph showing flame propagation speed versus the ratio of air to gas in a combustible mixture.

FIG. 2 graphically depicts the relationship between flame propagation speed and relative air-gas ratio. With valve 8 open, the air-gas ratio of $gm_2$ is 0.57/0.15 = 3.8. As seen on the graph, a ratio of 3.8 corresponds to a flame propagation speed of about 0.08 feet per second which is the same as the aforenoted flow velocity of 0.08 feet per second, whereby flashback will not occur. With valve 8 closed the air-gas ratio of $gm_2$ is (0.57 + 1.52)/0.15 = 14.0. As seen on the graph, a ratio of 14.0 corresponds to a flame propagation speed of about 0.30 feet per second which is the same as the aforenoted flow velocity of 0.30 feet per second of $gm_2$ with valve 8 closed, whereby flash-back will not occur.

Assume valve 8 is fully open and then is slowly closed. This will gradually introduce $a_2$ into $gm_2$, thereby leaning out the mixture and gradually increasing the ratio of air to gas in $gm_2$ above 3.8. When enough secondary air has been introduced to raise the ratio to about 10, FIG. 2, the flame propagation speed will be at a maximum, about 1.0 feet per second. If the ignition source is activated at about this time or has been continually energized throughout closing of valve 8, flash back will occur because the flow velocity is somewhere between 0.08 and 0.30 feet per second which is much less than the 1.0 feet per second speed of the travelling flame; thus a flame travels or flashes back from the outlet of flash-tube 24 to the burning zone and ignites the burner.

It will be seen from the graph that flash-back can occur before or after the ratio corresponding to the peak of the curve because even a rich mixture with a ratio as low as about 7 or a lean mixture with a ratio as high as about 13 still corresponds to a flame speed of about 0.4 feet per second which is greater than the 0.30 maximum flow velocity. Secondary air $a_2$ is thus controlled so as to vary the combustible mixture within the flash-tube and provide reliable and consistent flashback ignition because the air-gas ratio passes through a broad range of values corresponding to flame speeds greater than that necessary for flash-back.

An alternative to slowly closing valve 8, for example, would be to provide the upstream piping for $a_2$, from the burning zone back to orifice 10, of a sufficient volume such that when valve 8 is closed, $a_2$ is only slowly introduced into $gm_2$. Depending on the distance between the ignition source and the burning zone, $a_2$ should be introduced slowly enough so the flame has enough time to travel from the ignition source back to the burning zone before the air-gas ratio increases to a valve corresponding to a critically low flame speed in relation to the flow velocity in the other direction.

When the flame has flashed back to the burning zone, it stablizes above the bottom of the frustoconical portion of tube 18. This is because tube 18 is smaller than tube 24 and the flow velocity of $gm_1$ in tube 18 is 1.3 feet per second which exceeds not only the flame propagation speed corresponding to the 3.8 air to gas ratio of $gm_1$ but also the flame propagation speed corresponding to any of the mixture ratios noted in FIG. 2. The flame would also stablize above the bottom of the frustoconical portion of tube 18 when the flow velocity of air and gas issuing therefrom equals the flame propagation speed.

Operation of the automatically reignited burner is as follows. Heat or flame sensing means detects the absence of a flame in the burning zone and triggers a timer to perform the timed operations of opening valve 8 and then slowly closing valve 8 and energizing the ignition source, whereby the burner is automatically relit by flash-back ignition.

By using tube 24 as not only an exhaust tube but also as a flash-tube, ignition source 42 can be placed at the outlet of tube 24, downstream of the burning zone. The ignition source thus does not interfere with the heat transfer from the flame to the heat absorbing air, as it would if placed in or above the burning zone, and does not introduce the attendant error compensating factors in calibration due, for example, to various heat-sinking effects caused by construction and mounting means for placing the ignition source at the burning zone. Furthermore, since the ignition source is downstream and segregated from the burning zone, it is subjected to much lower temperatures and thus a resistance coil may be used, whereas a resistance coil at the burning zone would have a shortened life due to the elevated temperature thereat. In the specific embodiment disclosed, the resistance coil ignition source is about eight inches downstream of the burning zone and is at about room temperature in its de-energized state. An important advantage in the use of a resistance coil is that its period of energization can encompass the time span during which the air-gas ratio of $gm_2$ changes through its optimum values with respect to flame propagation speed, FIG. 2.

It has been found that when the heating value of high energy content gas, for example 900 BTU per cubic foot, is being measured, it may be desirable to provide capacity piping in the primary supply line to afford flame stabilization in the burning zone to improve consistency in recorded heating value. Capacity piping 44, shown in dotted line in FIG. 1, may be provided in supply line 4 together with a bypass line 46 having a valve 48. Prior to ignition, valve 48 is opened and $gm_1$ flows through line 46 while an ideal mixture with a normal air to gas ratio of 3.8 is created in capacity piping 44. Upon flash-back from igniter 42 to the burning zone, valve 48 is closed and the ideal explosive mixture reaches the burning zone to prevent lift-off of the flame from tube 18 or flash-back down tube 18.

It can easily be appreciated that the principles hereinbefore taught may be applied to other types of combustible fuel gas burners having a flash-tube, whereby to variably control the mixture in the flash-tube and enhance flash-back ignition.

What is claimed is:

1. A combustible fuel gas burner assembly comprising:
   feeder tube means;
   supply means feeding air and gas to one end of said feeder tube means for combustion at the other end of said feeder tube means to form a burning zone thereat;
   an exhaust tube having an inlet at said burning zone for carrying away the products of said combustion and, in the absence of said combustion, for carrying away the mixture of said air and gas;
   means for varying the ratio of air to gas in said mixture in said exhaust tube such that the flame propagation speed of said mixture in said exhaust tube changes through a spectrum of values at least one of which is greater than the flow velocity of said mixture in said exhaust tube;
   an ignition source spaced from said burning zone for igniting said mixture in said exhaust tube when said flame propagation speed is greater than said flow velocity, whereby said exhaust tube also serves as a flash-tube through which a flame travels from said ignition source to said burning zone;
   said feeder tube means and said exhaust tube being stationary with respect to each other during variance of said ratio of air to gas.

2. The burner assembly according to claim 1 wherein said means for varying said ratio in said exhaust tube is disposed in said supply means.

3. The burner assembly according to claim 2 wherein said means for varying said ratio controls the amount of said air fed to said burning zone.

4. The burner assembly according to claim 3 wherein said feeder tube means comprises a primary feeder tube and a secondary feeder tube and said supply means comprises a primary supply feeding gas and primary air to said burning zone through said primary feeder tube and a secondary supply feeding secondary air to said burning zone through said secondary feeder tube, said mixture in said exhaust tube comprising said gas plus said primary air plus said secondary air, and wherein said means for varying said ratio comprises control means disposed in said secondary supply for controlling the amount of said secondary air fed to said mixture.

5. A combustible fuel gas burner assembly comprising:
   supply means feeding air and gas to a burning zone for combustion thereat;
   an exhaust tube having an inlet at said burning zone for carrying away the products of said combustion and, in the absence of said combustion, for carrying away the mixture of said air and gas;
   means for varying the ratio of air to gas in said mixture in said exhaust tube such that the flame propagation speed of said mixture in said exhaust tube changes through a spectrum of values at least one of which is greater than the flow velocity of said mixture in said exhaust tube;
   an ignition source spaced from said burning zone for igniting said mixture in said exhaust tube when said flame propagation speed is greater than said flow velocity, whereby said exhaust tube also serves as a flash-tube through which a flame travels from said ignition source to said burning zone;
   wherein said means for varying said ratio in said exhaust tube is disposed in said supply means;
   said means for varying said ratio controls the amount of said air fed to said burning zone;
   said supply means comprises a primary supply feeding gas and primary air to said burning zone and a secondary supply feeding secondary air to said burning zone, said mixture in said exhaust tube comprising said gas plus said primary air plus said secondary air, and wherein said means for varying said ratio comprises control means disposed in said secondary supply for controlling the amount of said secondary air fed to said mixture;
   said control means comprises a valve operable between open and closed positions for controlling the amount of said secondary air in said mixture to thereby vary said ratio such that said flame propagation speed changes through said spectrum; and
   said primary supply comprises a primary line supplying said gas and said primary air to an elongated vertically extending primary tube to turn at a first cone at the top thereof, and wherein said secondary supply comprises a secondary line supplying said secondary air to an elongated vertically extending secondary tube concentrically surrounding said primary tube, said secondary air mixing with remaining gas unburned in said first cone to burn as a second cone, said first and second cones forming said burning zone, and wherein said exhaust tube concentrically surrounds said secondary tube and extends above said primary and secondary tubes, said exhaust tube being sealed at the top such that the products of combustion of said first and second cones are exhausted downwardly through said exhaust tube and, in the absence of said combustion, said mixture flows downwardly through said exhaust tube.

6. The burner assembly according to claim 5 wherein said ignition source is disposed adjacent the bottom of said exhaust tube and comprises a resistance coil having a period of energization which can encompass the time span during which said flame propagation speed changes through said spectrum in response to operation of said valve.

7. The burner assembly according to claim 6 adaptable for use in calorimeters and the like further comprising one or more additional elongated tubes concentrically surrounding said exhaust tube for carrying a heat absorbing medium whereby the heating value of said gas may be measured.

8. A combustible fuel gas burner assembly comprising:
  supply means feeding air and gas to a burning zone for combustion thereat;
  an exhaust tube having an inlet at said burning zone for carrying away the products of said combustion and, in the absence of said combustion, for carrying away the mixture of said air and gas;
  means for varying the ratio of air to gas in said mixture in said exhaust tube such that the flame propagation speed of said mixture in said exhaust tube changes through a spectrum of values at least one of which is greater than the flow velocity of said mixture in said exhaust tube;
  an ignition source spaced from said burning zone for igniting said mixture in said exhaust tube when said flame propagation speed is greater than said flow velocity, whereby said exhaust tube also serves as a flash-tube through which a flame travels from said ignition source to said burning zone;
  wherein said supply means comprises a primary supply feeding gas and primary air to said burning zone and a secondary supply feeding secondary air to said burning zone, said mixture in said exhaust tube comprising said gas plus said primary air plus said secondary air; and
  wherein said primary supply comprises a primary line supplying said gas and said primary air to an elongated vertically extending primary tube to burn as a first cone at the top thereof, and wherein said secondary supply comprises a secondary line supplying said secondary air to an elongated vertically extending secondary tube concentrically surrounding said primary tube, said secondary air mixing with remaining gas unburned in said first cone to burn as a second cone, said first and second cones forming said burning zone, and wherein said exhaust tube concentrically surrounds said secondary tube and extends above said primary and secondary tubes, said exhaust tube being sealed at the top such that the products of combustion of said first and second cones are exhausted downwardly through said exhaust tube and, in the absence of said combustion, said mixture flows downwardly through said exhaust tube.

* * * * *